United States Patent [19]

Eisman et al.

[11] Patent Number: 5,154,177
[45] Date of Patent: Oct. 13, 1992

[54] MYOGRAPHIC ELECTRODE

[76] Inventors: Eugene Eisman, 3209 N. Summit Ave., Milwaukee, Wis. 53211; Jeannette Tries, 3125 S. 57th St., Milwaukee, Wis. 53219

[21] Appl. No.: 685,418

[22] Filed: Apr. 12, 1991

[51] Int. Cl.⁵ ............................................. A61B 5/0488
[52] U.S. Cl. .................................. 128/642; 128/733; 128/778
[58] Field of Search ................. 128/642, 733, 778, 788

[56] References Cited

U.S. PATENT DOCUMENTS

| | | | |
|---|---|---|---|
| 2,541,520 | 2/1951 | Kegel | 128/778 |
| 3,749,100 | 7/1973 | Mosel | 128/788 |
| 4,396,019 | 8/1983 | Perry, Jr. | 128/733 |
| 4,515,167 | 5/1985 | Hochman | 128/788 X |
| 4,785,828 | 11/1988 | Maurer | 128/788 |
| 4,895,363 | 1/1990 | Plevnik et al. | 272/93 |

FOREIGN PATENT DOCUMENTS

| | | | |
|---|---|---|---|
| 2601254 | 1/1988 | France | 128/788 |
| 9012617 | 11/1990 | World Int. Prop. O. | 128/642 |

OTHER PUBLICATIONS

Bradley et al., "Sphincter Electromyography" Urologic Clinics of North America, vol. 1, No. 1, Feb. 1974, pp. 69-79.
Instructional Sheet for "Femina" Pelvic Floor Muscle (Kegel) Training Weights for Women, Dacomed Corporation.

Primary Examiner—Lee S. Cohen
Attorney, Agent, or Firm—Quarles & Brady

[57] ABSTRACT

An electrode assembly measures myographic signals on the superior side of the pelvic floor muscles, viz., the urogenital diaphragm or the puborectalis muscle, under a state of physiological contraction for various retention forces. The electrode assembly has an insulating support having a conical end. The assembly is inserted through the vagina or anal canal so that electrodes on the conical face rest against the superior side of the pelvic floor muscles to receive electromyographic signals. The weight of the assembly may be selected to provide various amounts of muscular reaction. An insertion guide provides an indication of the orientation of the electrodes as positioned by the insertion guide.

8 Claims, 1 Drawing Sheet

MYOGRAPHIC ELECTRODE

FIELD OF THE INVENTION

The present invention relates to an electrode assembly for measuring electrical signals produced by muscles of the pelvic floor and, in particular, by muscles of the superior surface of the levator muscle plate which supports the bladder neck, rectum, and vagina in the appropriate anatomical position. These muscles function in conjunction with the urinary and anal sphincters during the storage and elimination of feces and urine and are therefore part of the continence mechanism.

BACKGROUND OF THE INVENTION

Certain forms of incontinence in women have been linked to poor muscle tone in the pubococcygeus or pelvic floor muscles. The muscles extend from the pubic bone to the coccyx; they interdigitate with the sphincter muscles that encircle the anal canal and the urethra and they surround and underlie the vagina. Exercises of the pelvic floor muscles have been evaluated and shown to be effective in improving muscle tone and eliminating incontinence. During childbirth the pelvic floor muscles and their nerve supply are subject to considerable stress. Exercise of the pelvic floor muscles is also considered desirable in preparing for childbirth and recovery therefrom.

Although pelvic floor muscles are striated and innervated by the somatic nervous system, voluntary control of them is often limited. Following trauma to the muscles themselves, or their innervation, such control may be even less available.

One device for providing exercise to the pelvic floor muscles is described in U.S. Pat. No. 4,895,363 to Plevnik et al. and entitled "Set of Parts and Methods for Testing and/or Strengthening Pelvic Floor Muscles." According to the method of this patent, one of a set of weights "cones" is inserted into the vagina and held in place for a period of time. The weight of the cone against the pelvic floor muscles provides a sensation that the cone is slipping out which in turn causes the pelvic floor muscles to contract and also sensitizes the user to this contraction so as to be able to assist in voluntary control of the contraction. Different cones of different weights are used as a means of graduated muscle training and as a means of evaluating muscle tone.

As noted by Plevnik, the contraction of the pelvic floor muscles in holding the cones in place may be accompanied by an unconscious contraction of the abdominal muscles which creates a pressure, forcing the cone out. It is believed that the failure of some patients to benefit from exercises using the Plevnik cone, in treating their stress incontinence, may result from their continued habit of contracting their abdominal muscles along with their pelvic floor muscles. Thus interaction of the abdominal muscles and the pelvic floor muscles also complicates the use of the Plevnik devices in evaluating muscle tone.

SUMMARY OF THE INVENTION

In the present invention, two electrodes are attached to an insulating support which fits through an opening in the pelvic floor muscles, such as the vagina or the anal canal, and after insertion allows the muscles of the vagina or the anal canal to assume their undilated condition. The end of the insulating support facing the superior surfaces of the pelvic floor muscles is generally conical and the electrodes are placed on this conical face.

It is one object of the invention to allow quantitative, diagnostically significant measurement of the muscle activity of the puborectalis and pubococcygeus muscles, which are all subdivisions of the levator ani group. The electrodes allow detection of the myographic signals indicating activity at this muscle group and thus also allow quantitative measurement of that activity. The ability of the insulating support to fit completely through these openings in the pelvic floor muscles allows the myographic measurements to be obtained with the openings in the diagnostically important undilated state and from the preferred superior side of the pelvic floor muscles. The shape of the insulating support is such as to guide the electrodes naturally to the desired, specific region of the pelvic floor muscles. Because the electrodes are small, they record muscle activity that is relatively specific to the pelvic floor muscles and in isolation from the abdominal muscles. The ability to measure and display, as biofeedback signals, activity of the levator plate separate from activity of the abdominal muscles is important in training patients to use and exercise the pelvic floor muscles efficiently. This ability is also important for the accurate evaluation of pelvic floor muscle tone and contractile ability.

It is another object of the invention to provide an electrode assembly that may be used comfortably and conveniently in a variety of positions, and during various procedures which evaluate the functional integrity of the pelvic floor muscles during storage and evacuation maneuvers. Positioning the insulating support above the levator plate avoids discomfort that might otherwise be caused by the electrode assembly. It also avoids any protruding structures of a probe that would interfere with activities of a patient. The pelvic floor muscles hold the electrode assembly in position even when the patient is standing and thus allows for the quantification of muscle activity in functional positions in which patients are likely to become incontinent. Thus, it is believed that training in such positions would facilitate the kind of muscle control that would generalize most readily to the life situation.

The insulating support may include various weights for controlling the total weight of the insulating support and hence the contact pressure between the conical end of the support and the underlying pelvic floor muscle.

It is thus another object of the invention to provide a range of quantitative measurements reflecting muscle activity under various degrees of exertion and to permit the user to learn to isolate the contraction of the pelvic floor muscles from contraction of the abdominal muscles under various degrees of muscle exertion.

An insertion guide may be employed having fingers for receiving and holding the insulating support for insertion through the vagina or anal canal and for ensuring that the electrodes are given a particular orientation.

It is therefore another object of the invention to permit the orientation of the electrodes on the superior surface of the sphincter to be directed in a particular manner to ensure the accuracy and reproducibility of the measurements of myographic signals. The foregoing, and other objects and advantages of the invention, will appear from the following description. In the description, reference is made to the accompanying drawings which form a part hereof, and in which there is shown, by way of illustration, a preferred embodiment

DETAILED DESCRIPTION OF THE INVENTION

Figure 1:
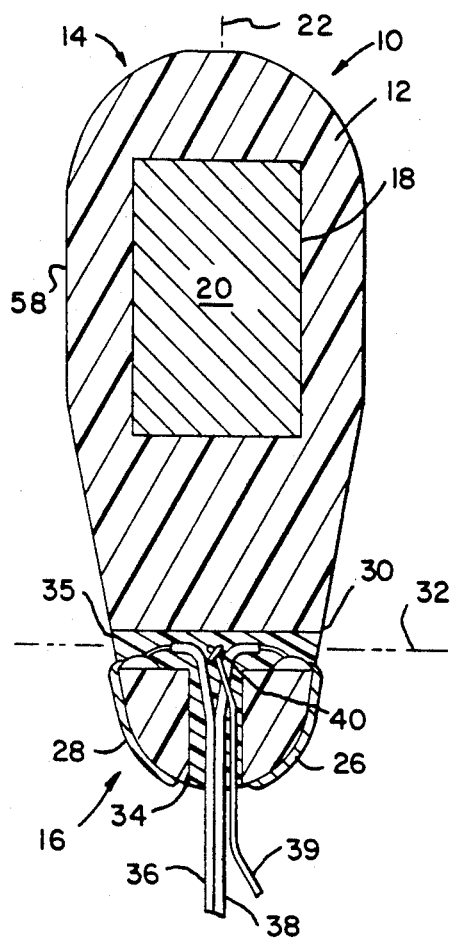
FIG. 1 is a cross-sectional, elevational view of the electrode assembly of the present invention.

Referring to FIG. 1, an electrode assembly 10 includes a generally cylindrical insulating support 12 having a first rounded end 14 and a second conical end 16. The insulating support 12 is manufactured preferably from a thermoplastic material suitable for use in medical applications. A cavity 18, approximately centered within the insulating support 12, holds a weight 20 of predetermined mass as will be described below.

The insulating support 12 is generally symmetrical about a longitudinal axis 22 extending from the center of the rounded end 14 to the apex 24 of the conical end 16. Positioned in opposition around the longitudinal axis 22 on the face of the conical end 16 are longitudinally extending electrodes 26 and 28. In the preferred embodiment, electrodes 26 and 28 are adhesive-coated, copper foil pressed onto the face of conical end 16 so as to be substantially flush with the surface of conical end 16 and to conform to its slight curvature. The electrodes 26 and 28 do not extend all the way to the apex 24, but rather stop short of the apex 24 at their lower ends so as to maintain electrical isolation from each other.

A hole 30 drilled along a transverse axis 32 through the insulating support 12, along the base of the cone defining the conical end 16 and through the longitudinal axis 22, forms a channel from the upper end of electrode 22 to the upper end of electrode 26.

A second hole 34 proceeding longitudinally along axis 22 from the apex 24 to the center of hole 30 connects with hole 30, to allow a conductor 36 to be attached to the upper end of electrode 28 and threaded through hole 30 to hole 34 to ultimately exit from the apex 24 of the conical end 16. A second conductor 38 similarly attaches to the upper end of electrode 26 and passes through hole 30 to hole 34, also to exit from the apex 24 of the conical end 16. Conductors 36 and 38 are preferably 32 gauge, 5 strand copper wire with an insulating covering as is understood in the art, and are soldered to the upper ends of electrodes 28 and 26, respectively, fitting within the ends of hole 30. The holes and 34 are filed with a medical grade silicone rubber 35.

A monofilament nylon filament 39 is fastened by means of a knot 40 resting against the upper edge of hole 34 at its junction with hole 30 to allow the filament 39 to be used to remove the electrode assembly 10 from the sphincter after it is positioned, as will be described.

Figure 2:
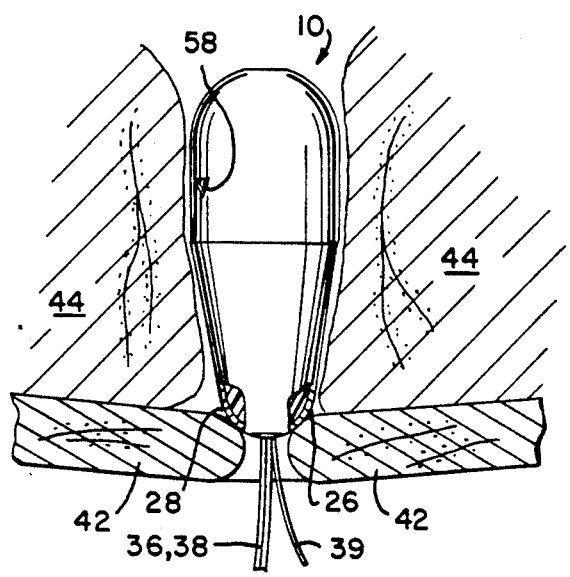
FIG. 2 is a partial cross sectional view of the electrode assembly of FIG. 1 in place on the superior side of the undilated vagina.

Referring to FIG. 2, the electrode assembly 10 rests on the superior surface of the pelvic floor muscles 42 as generally positioned by the walls of the vagina 44. The surfaces of electrodes 28 and 26 are thus naturally guided to the specific location of the superior surface of the pelvic floor muscles 42 and held in contact with that surface by the weight of the electrode assembly 10 and the action of the abdominal muscles (not shown) through the walls of the vagina 44. It will be understood that the electrode assembly 10 may alternatively also be positioned in the anal canal for measurement of the pelvic floor muscles 42 in the vicinity of the anal canal. Henceforth, openings in the pelvic floor muscles will be held to mean both the openings of the vagina and that of the anal canal. The conductors 36 and 38 and the filament 39 pass through the opening of the pelvic floor muscles 42, the former for connection to myographic detecting equipment, as is generally understood in the art, and the latter for use in removing the electrode assembly 10. It is noted that the electrode assembly 10 in this position provides myographic signals for the pelvic floor muscles 42 in an undilated, physiological state. Further, only the conductors 36 and 38 and the filament 39, all of which are flexible, protrude from the sphincter 42, thus improving the patient comfort and mobility.

During use, the electrode assembly 10 is inserted through the vagina 44 or anal canal to rest just above the pelvic floor muscle 42 and myographic measurements may be made with the patient in a variety of postures and activities. A particular electrode assembly 10 may be removed and replaced with an electrode assembly 10 having a heavier or lighter weight 20 to obtain additional myographic data under a different force of contraction of the sphincter 42 and is produced by the differing weights 20 of the electrode assemblies 10.

Figure 3:
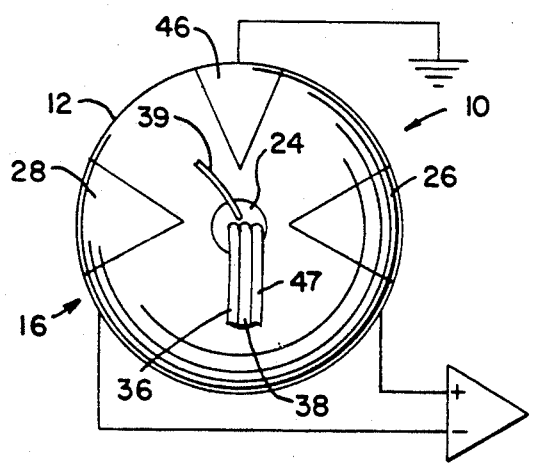
FIG. 3 is a bottom plan view of a second embodiment of the electrode assembly of FIG. 1 having three electrodes.

Referring to FIG. 3, in a second embodiment, an additional ground electrode 46 may be positioned between the electrodes 26 and 28 also extending generally longitudinally on the surface of the conical end 16 of the insulating support 12.

A third hole (not shown) may be used to connect a third conductor 47 to this ground electrode 46 in a manner similar to that of the other electrodes 36 and 38. The ground electrode 46 provides an additional signal reference between the signals provided by electrodes 26 and 28 that may be used to reduce the effect of electrical noise on the low-powered myographic signal, as is generally understood in the art.

Figure 4:
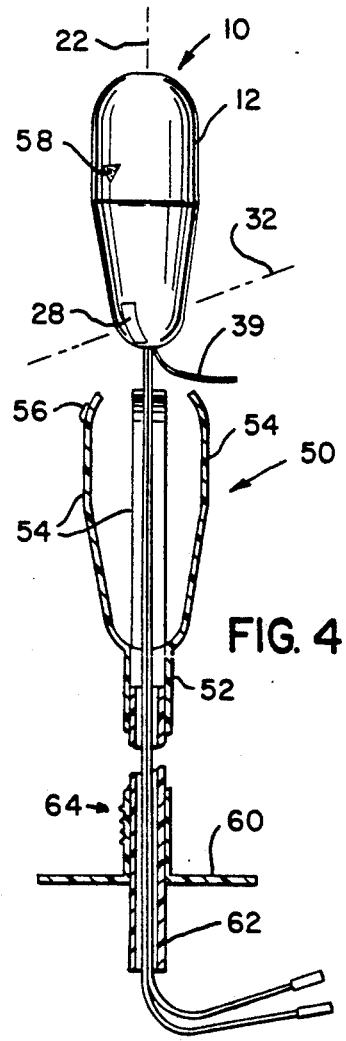
FIG. 4 is a cross-sectional view of an insertion guide with the electrode assembly of FIG. 1 showing the fiducial marks used to align each.

Referring to FIG. 4, the orientation of the transverse axis 32, defined by the locations of the electrodes 28 and 26, may be controlled by means of an insertion guide 50. Insertion guide 50 (the latter not visible in FIG. 4) is comprised generally of a tubular handle 52 having at one end a plurality of flexible fingers 54 for receiving the electrode assembly 10, when the longitudinal axis 22 of the electrode assembly 10 is coaxially aligned with the axis of tubular handle 52. The fingers 54 surround the insulating support 12 with the conical end 16 closest to the tubular handle 52 and with the conductors 36 and 38 passing through the tubular handle 52 and out through its opposite end.

The tubular handle 52 and fingers 54 are constructed from a resilient material and outwardly biased by the insertion of the electrode assembly 10, thereby grasping the electrode assembly 10 when it is inserted into the fingers 54. One finger 54 contains a fiducial mark 56 which may be aligned with a corresponding fiducial mark 58 on the outer portions of the insulating support 12 when the electrode assembly 10 is grasped by the fingers 54. The fiducial mark 56 is located with respect to the wings of a T-handle 60 formed in the end of tubular handle 52 opposed to the fingers 54. The orientation of the T-handle 60 may be determined tactilely, and the T-handle 60 may be used to align the transverse axis 32 of the electrode assembly 10 when the electrode assembly 10 is properly aligned with the insertion guide 50 by aligning fiducial marks 56 and 58. A co-axial tube 62 fits within the T-handle 52 to slide therein and is of sufficient length to protrude from the end of the tubular handle 52 having the T-handle 60 by the length of the electrode assembly 10 when the electrode assembly 10 is in place within the fingers 54 and has its apex 24 resting against the end of tube 52.

Referring also to FIG. 2, insertion of the electrode assembly 10 is accomplished by grasping the tubular handle 52 and the T-handle 60 and inserting the electrode assembly 10 as held by fingers 54 through the vagina or anal canal. Although the electrode assembly 10 is generally self-locating to the superior surface of the pelvic floor muscle 42, graduations on tubular handle 52 may be used to gauge the insertion depth of the electrode assembly 10. Once the electrode assembly 10 is in position on the superior surface of the pelvic floor muscle 42, the tubular handle 52 and the attached fingers 54 may be removed, leaving the electrode assembly 10 in place. This removal is facilitated by holding tube 62 fixed with respect to the pelvic floor muscle 42 while the tubular handle 52 is withdrawn, the upper end of tube 62 serving to prevent the electrode assembly 10 from following the fingers 54.

The above description has been that of a preferred embodiment of the present invention. It will occur to those who practice the art that many modifications may be made without departing from the spirit and scope of the invention. For example, additional electrodes may be placed on the conical surface 16 to obtain additional signal information. Further, it will be apparent that this electrode assembly will be of particular value for telemetry applications where the conductors are replaced with radio links. In order to apprise the public of the various embodiments that may fall within the scope of the invention, the following claims are made.

We claim:

1. An electrode assembly for electromyographic measurements of the muscles of the pelvic floor having an opening, comprising:
    an insulating support means having a first generally conical end symmetric about a longitudinal axis, the support means for being received completely through the opening in the pelvic floor muscles to allow contraction of the opening and to be positioned with the conical end facing the superior side of the pelvis floor muscles;
    a first and second longitudinally extending electrode disposed symmetrically about the longitudinal axis on the surface of the conical end for receiving myographic electrical signals from the pelvic floor muscles when the conical end contacts the pelvic floor muscles and;
    electrical signal path means for communicating the myographic electrical signals received by the first and second electrodes to myographic measuring equipment.

2. An electrode assembly according to claim 1 wherein the insulating support means includes a weight adjustment means for fixing the total weight of the electrode assembly to a predetermined value and hence controlling the contact pressure between the conical end and the pelvic floor muscles.

3. An electrode assembly according to claim 1, including a first and second flexible conductor attached to the first and second electrode, respectively, for providing an electrical path between the first and second electrode and myographic measuring equipment outside the opening.

4. An electrode assembly according to claim 3, wherein the first and second conductors are received by channels inside the insulating support means and exit from the insulating support means from the apex of the conical end.

5. An electrode assembly according to claim 1, including a flexible cord having one end attached to the apex of the conical end, for assisting in removal of the insulating support means from the opening.

6. An electrode assembly according to claim 1, including a third longitudinally extending electrode disposed symmetrically about the longitudinal axis on the surface of the conical end between the first and second electrodes, for receiving myographic electrical signals from the opening when the conical end contacts the opening.

7. An electrode assembly for electromyographic measurements of the muscles of the pelvic floor, having an opening, comprising:
    an insulating support means having a first generally conical end symmetric about a longitudinal axis, the support means for being received completely through the opening to allow contraction of the opening and to be positioned with the conical end facing to the superior side of the pelvic floor muscles;
    a first and second longitudinally extending electrode disposed symmetrically about the longitudinal axis on the surface of the conical end and defining a transverse axis for receiving myographic electrical signals from the opening along the transverse axis when the conical end contacts the opening;
    electrical path signal means for communicating the myographic electrical signals received by the first and second electrodes to myographic measuring equipment;
    an insertion guide having finger means for slideably receiving the insulating support means along its longitudinal axis in predetermined orientation with respect to the transverse axis, the finger means attached to a first end of a longitudinal handle for guiding the insulating support means through the opening when the insulating support means is retained in the finger means; and
    a tactile indicator on the second end of the handle for indicating the orientation of the transverse axis with respect to the opening.

8. An electrode assembly according to claim 7 including a first and second flexible conductor attached to the first and second electrode, respectively, for providing an electrical path between the first and second electrode and myographic measuring equipment outside the opening; and
    wherein the handle is hollow for receiving the first and second flexible conductors when the insulating support means is guided through the opening.

* * * * *